United States Patent
Kawazoe et al.

(10) Patent No.: US 6,889,400 B2
(45) Date of Patent: May 10, 2005

(54) CLEANING MEMBER FOR MEDICAL TUBES, POROUS MEMBER FOR CLEANING TREATMENT APPLIANCE INSERTION LUMEN OF ENDOSCOPE, AND CLEANING APPARATUS FOR CLEANING TREATMENT APPLIANCE INSERTION LUMEN OF ENDOSCOPE

(75) Inventors: Kaoru Kawazoe, Nagasaki-ken (JP); Koji Yoneyama, Nagoya (JP); Hiroaki Kamiya, Kasugai (JP)

(73) Assignee: One Step Co., Ltd., Kasugai (JP)

( * ) Notice: Subject to any disclaimer, the term of this patent is extended or adjusted under 35 U.S.C. 154(b) by 118 days.

(21) Appl. No.: 10/400,514

(22) Filed: Mar. 28, 2003

(65) Prior Publication Data

US 2003/0213074 A1 Nov. 20, 2003

(30) Foreign Application Priority Data

Mar. 28, 2002 (JP) ........................................ 2002-091332

(51) Int. Cl.⁷ .............................................. B08B 9/055
(52) U.S. Cl. ................. 15/3.5; 15/104.061; 15/104.062
(58) Field of Search ............................. 15/3.5, 104.061, 15/104.062

(56) References Cited

U.S. PATENT DOCUMENTS

| | | | |
|---|---|---|---|
| 597,185 A | * | 1/1898 | Huebner ...................... 15/3.5 |
| 4,383,346 A | * | 5/1983 | Bochinski et al. ...... 15/104.061 |
| 4,406,030 A | * | 9/1983 | Platts .................... 15/104.061 |
| 4,550,466 A | * | 11/1985 | Schmitz ................. 15/104.061 |
| 5,640,734 A | * | 6/1997 | Kuwashima ................. 15/3.5 |
| 6,045,623 A | | 4/2000 | Cannon |
| 6,272,713 B1 | * | 8/2001 | Lotwin ................... 15/104.061 |

FOREIGN PATENT DOCUMENTS

| | | |
|---|---|---|
| JP | 11-197092 | 7/1999 |
| JP | 2001-070243 | 3/2001 |
| WO | WO 92/02310 A1 | 2/1999 |

* cited by examiner

*Primary Examiner*—Robert J. Warden, Sr.
*Assistant Examiner*—Shay Balsis
(74) *Attorney, Agent, or Firm*—Burns, Doane, swecker & Mathis, L.L.P.

(57) ABSTRACT

The cleaning member for a medical tube is shaped like a spherical body having a porous fibrous structure formed of a large number of superfine fibers aggregated and intertwined three-dimensionally. The spherical body moves along a lumen surface of the medical tube together with a cleaning liquid, with the cleaning member wiping and cleaning the lumen surface of the medical tube.

The porous member for cleaning the treatment appliance insertion lumen of the endoscope is formed approximately spherically by molding a large number of superfine fibers. The porous member can be swelled with an aqueous cleaning liquid. When the porous member swells, the outer diameter of the porous member becomes larger than the inner diameter of a treatment appliance insertion lumen of an endoscope to be cleaned. Further because the porous member deforms, the porous member can be inserted into the treatment appliance insertion lumen of the endoscope. Moreover, the aqueous cleaning liquid flowing into the treatment appliance insertion lumen of the endoscope allows the porous member to move in contact with an inner wall of the lumen.

18 Claims, 10 Drawing Sheets

US 6,889,400 B2

CLEANING MEMBER FOR MEDICAL TUBES, POROUS MEMBER FOR CLEANING TREATMENT APPLIANCE INSERTION LUMEN OF ENDOSCOPE, AND CLEANING APPARATUS FOR CLEANING TREATMENT APPLIANCE INSERTION LUMEN OF ENDOSCOPE

BACKGROUND OF THE INVENTION

Field of the Invention

The present invention relates to a cleaning member for medical tubes such as an endoscope, a laparoscope, and the like having a lumen surface and a feeding instrument for feeding the cleaning member. More particularly, the present invention relates to a cleaning porous member, a cleaning instrument, and a cleaning apparatus for cleaning a treatment appliance insertion lumen of the endoscope.

As the method of cleaning the endoscope which is used to make an examination of the internal organs or the like, the lumen surface of the endoscope is brushed manually. A cleaning apparatus capable of automatically brushing the lumen surface of the endoscope is disclosed in each of Japanese Patent Application Nos. 11-197092 (hereinafter referred to as conventional art 1) and 2001-70243 (hereinafter referred to as conventional art 2).

In the cleaning instrument of the conventional art 1, a plurality of brushes are movably connected to each other with a flexible fibrous material. The cleaning instrument is inserted into a duct (treatment appliance insertion lumen) of the endoscope and moved under a pressure inside the duct by cleaning water to brush the inner surface of the duct. However, because the outer diameter of the brush is smaller than the inner diameter of the duct, the tip of the brush rubs the inner surface of the duct irregularly and lightly. Thus the brush is capable of removing removable pollutants of secretion such as mucus, blood, a tissue piece, and the like comparatively easily from the inner surface of the duct, but has a problem in the removal of viruses, bacteria, and various microbes. The brushes connected to each other have a smaller diameter than the inner diameter of the duct. Therefore there is a possibility that the cleaning instrument, namely, the brushes clog in the duct because a bridge phenomenon occurs, i.e., the brushes overlap each other at a stepped portion, inside the duct of the endoscope, between adjacent parts of the duct having different diameters and a curved portion.

In the conventional art 2 proposed by the present inventors, the spherical brush and a cleaning liquid are moved by a suction force to remove not only secretion such as mucus, blood, a tissue piece, and the like, but also viruses, bacteria, and various microbes from the inner surface of the duct with the brush.

In view of the above-described problems, the present inventors have made investigations energetically. Therefore it is an object of the present invention to provide a cleaning member for medical tubes and a feeding instrument for feeding the cleaning member capable of cleaning a lumen of an endoscope effectively and reliably and improve the construction of the feeding instrument to allow the feeding instrument to be used easily and conveniently and handled conveniently

SUMMARY OF THE INVENTION

In accordance with the present invention, the objects described above are achieved by a cleaning member for a medical tube shaped like a spherical body, having a porous fibrous structure formed of a large number of superfine fibers aggregated and intertwined three-dimensionally, which moves along a lumen surface of said medical tube together with a cleaning liquid, while said cleaning member is wiping and cleaning said lumen surface of said medical tube.

Also, in accordance with the present invention, the objects described above are achieved by a cleaning instrument for a medical tube comprising a cleaning member-holding plate having a plurality of holding-holes for holding a plurality of cleaning members fitted in said holes respectively, with said holding-holes disposed circumferentially at equal intervals; and a plurality of cleaning members shaped like a spherical body, having a porous fibrous structure formed of a large number of superfine fibers aggregated and intertwined three-dimensionally, which moves along a lumen surface of said medical tube together with a cleaning liquid, while said cleaning member is wiping and cleaning said lumen surface of said medical tube, and said cleaning members are accommodated in said through-holes respectively.

Also, in accordance with the present invention, the objects described above are achieved by a porous member, for cleaning a treatment appliance insertion lumen of an endoscope, which is formed approximately spherically by molding a large number of superfine fibers; can be swelled with an aqueous cleaning liquid; an outer diameter thereof becomes larger than an inner diameter of said lumen to be cleaned, when said porous member swells; can be inserted into said lumen owing to a deformation thereof; and is movable in contact with an inner wall of said lumen by said aqueous cleaning liquid flowing into said lumen.

Also, in accordance with the present invention, the objects described above are achieved by a cleaning instrument for cleaning a treatment appliance insertion lumen of an endoscope comprising a cartridge body having a plurality of through-holes disposed equiangularly or at equal intervals; and porous members, for cleaning a treatment appliance insertion lumen of an endoscope, which are formed approximately spherically by molding a large number of superfine fibers; can be swelled with an aqueous cleaning liquid; an outer diameter thereof becomes larger than an inner diameter of said lumen to be cleaned, when said porous member swells; can be inserted into said lumen owing to a deformation thereof; and are movable in contact with an inner wall of said lumen by said aqueous cleaning liquid flowing into said lumen, and said porous members are accommodated in a plurality of said through-holes respectively.

Also, in accordance with the present invention, the objects described above are achieved by a cleaning apparatus for cleaning a treatment appliance insertion lumen of an endoscope comprising a cleaning instrument, for cleaning said treatment appliance insertion lumen of said endoscope, having a cartridge body provided with a plurality of through-holes disposed equiangularly or at regular intervals; and lumen-cleaning porous members accommodated in said through-holes respectively; and a feeding instrument, for feeding said lumen-cleaning porous members, having a cleaning instrument accommodation portion removably accommodating said cleaning instrument, a cleaning liquid inflow side guide path communicating with one end of one through-hole of said cartridge body of said cleaning instrument accommodated in said cleaning instrument accommodation portion, a cleaning liquid outflow side guide path communicating with the other end of said through-hole, an endoscope-end mounting portion disposed at an end of said cleaning liquid outflow side guide path, and a cartridge-driving mechanism for operating said cartridge body in such a way that each through-hole of said cartridge body communicates with said cleaning liquid inflow side guide path and said cleaning liquid outflow side guide path.

DETAILED DESCRIPTION OF THE PREFERRED EMBODIMENTS

An example of the embodiment of the cleaning member for medical tubes of the present invention and the cleaning member-feeding instrument of the present invention will be described below with reference to drawings.

FIGS. 1 through 4 are schematic sectional views each showing a cleaning member for medical tubes of the present invention.

The cleaning member for a medical tube of the present invention is shaped like a spherical body having a porous fibrous structure formed of a large number of superfine fibers aggregated and intertwined three-dimensionally. The spherical body moves along a lumen surface of the medical tube together with a cleaning liquid, with the cleaning member wiping and cleaning the lumen surface of the medical tube.

The cleaning member for the medical tube of the present invention is shaped like a spherical body made of only intertwined superfine fibers having minute concavities and convexities formed thereon. The cleaning member moves along the lumen surface of the medical tube together with the cleaning liquid, with the cleaning member rotating at small angles and wiping and cleaning the lumen surface of the medical tube.

The cleaning member for a medical tube of the present invention is shaped like a spherical body made of an elastic material having minute grooves, holes or concavities and convexities formed on its surface. The cleaning member moves along the lumen surface of the medical tube together with the cleaning liquid, with the cleaning member rotating at small angles and wiping and cleaning the lumen surface of the medical tube.

The cleaning member for a medical tube of the present invention is shaped like a spherical body having superfine fibers having minute concavities and convexities formed thereon and an elastic material, having an elastic force, contained at the center of the spherical body. The cleaning member moves along the lumen surface of the medical tube together with the cleaning liquid, with the cleaning member rotating at small angles and wiping and cleaning the lumen surface of the medical tube.

The cleaning member for the medical tube is made of a porous member for cleaning a treatment appliance insertion lumen of an endoscope.

Figure 1:
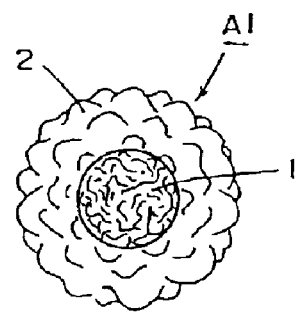
FIG. 1 is a schematic sectional view showing an example of a cleaning member for medical tubes of the present invention.

A cleaning member A1 of an embodiment shown in FIG. 1 is shaped like a spherical body. A cleaning member A1 of an embodiment has a hard dense core part and a flexible rough part covering said hard dense core part. A cleaning member A1 has a double construction including a hard dense core material 1 having a porous fibrous structure and a flexible rough surface material 2, formed on the outer surface of the core material 1, having a porous fibrous structure. Both the core material 1 and the surface material 2 have the porous fibrous structure in which an enormous number of superfine fibers are aggregated and intertwined with one another three-dimensionally. The porous fibrous structure is cotton-like. That is, the porous fibrous structure is made of not less than one million flat superfine fibers, each having a sectional area of less than 10 $\mu m^2$, aggregated and intertwined with one another three-dimensionally. It is desirable to use multi-layer division-type superfine fibers composed of an ethylene vinyl alcohol copolymer and polyethylene terephthalate, a copolymer containing acrylic amid as its one component, and polylactic acid.

Cleaning of the duct of the endoscope will be described below as an example of cleaning of the medical tube.

As described above, the cleaning member is shaped like a spherical body having the porous fibrous structure having the core material 1 and the surface material 2. Therefore in cooperation with an elastic action of the core material 1, the superfine fibers present on the surface of the sphere are pressed against the surface of the duct of the endoscope. Consequently the cleaning member wipes and rubs off (chips off) secretions such as mucus, blood, tissue pieces, viruses, bacteria, and pollutants (including adsorbed oily content) such as various microbes from the surface of the duct of the endoscope and encloses them in porous portions between the fibers. Because the cleaning member is porous, it is flexible in conformity to different diameters (inner diameters) of the duct of the endoscope and a stepped portion between adjacent parts of the duct having different diameters, and curves (angles). Thus the cleaning member moves in the duct without clogging therein, while it is rotating at small angles in dependence on a degree of a resistance applied to the cleaning member from the surface of the duct of the endoscope.

Thus the cleaning member moves together with the cleaning liquid in various directions while it is rotating at small angles in dependence on a degree of a resistance applied to the cleaning member from the surface of the duct of the endoscope against which the cleaning member is pressed. Thereby after the endoscope is used, i.e., after examination terminates, the cleaning member efficiently wipes and rubs the entire surface in the duct to thereby wipe off and rub off not only secretions such as mucus, blood, tissue pieces, but also viruses, bacteria, and pollutants such as various microbes that are difficult to remove from the surface of the duct in the endoscope.

Figure 2:
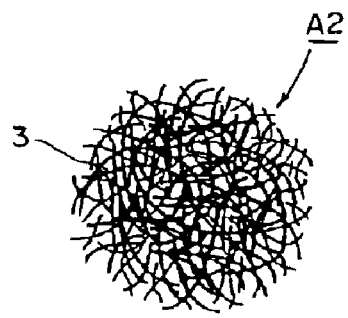
FIG. 2 is a sectional view showing another example of the cleaning member for medical tubes of the present invention.

A cleaning member A2 of the embodiment shown in FIG. 2 is shaped like a spherical body made of intertwined superfine fibers 3 having minute concavities and convexities formed thereon. The cleaning member A2 moves together with the cleaning liquid in various directions, while it is rotating at small angles in dependence on the degree of a resistance applied to the cleaning member from the surface of the duct of the endoscope against which the cleaning member is pressed. Thereby after the endoscope is used, i.e., after examination terminates, the cleaning member A2 efficiently wipes and rubs the entire surface of the duct to thereby wipe off and rub not only secretions such as mucus, blood, tissue pieces, but also viruses, bacteria, and pollutants such as various microbes that are difficult to remove from the surface of the duct of the endoscope, with them attaching to the inside of the minute concavities and convexities of the fibers of the cleaning member A2. At this time, a suction force causes the cleaning liquid such as an enzyme cleaning agent to constantly flow inside the spherical cleaning member A2. Thus the cleaning member A2 cleans the pollutants that have attached to the fibers by wiping off and rubbing off the pollutants into the cleaning liquid. Therefore the pollutants that have been removed from the surface of the duct do not attach thereto. That is, the cleaning member cleans them efficiently.

Figure 3:
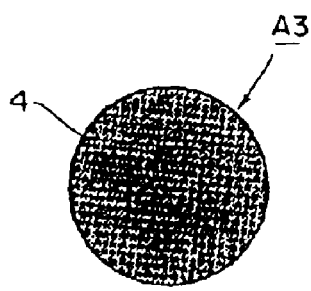
FIG. 3 is a sectional view showing another example of the cleaning member for medical tubes of the present invention.

A cleaning member A3 of the embodiment shown in FIG. 3 is shaped like a spherical body made of sponge or an elastic material 4 having minute grooves, holes or concavities and convexities formed on its surface. The cleaning member A3 moves together with the cleaning liquid in various directions, while it is rotating at small angles in dependence on a degree of a resistance applied to the cleaning member from the surface of the duct of the endoscope against which the cleaning member is pressed. Thereby after the endoscope is used, i.e., after examination terminates, owing to the elastic force of the sphere and the area of contact between the surface of the duct and the sphere increased owing to the formation of the minute grooves, holes or concavities and convexities present on its surface, the cleaning member A3 wipes and rubs the entire surface in the duct efficiently to thereby wipe off and rub off not only secretions such as mucus, blood, tissue pieces, but also viruses, bacteria, and pollutants such as various microbes that are difficult to remove from the surface of the duct of the endoscope. At this time, the sphere (cleaning member A3) moves, while it is rotating in dependence on a degree of a resistance applied thereto from the surface of the duct of the endoscope against which the cleaning member A3 is pressed. Therefore the cleaning member A3 washes off the pollutants that have attached to the surface thereof into the cleaning liquid, thus preventing the pollutants from dogging on the surface thereof. That is, the cleaning member A3 is always capable of cleaning the surface of the duct efficiently and reliably.

Figure 4:
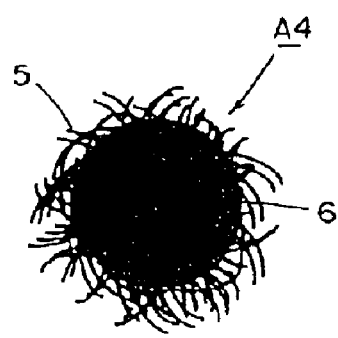
FIG. 4 is a sectional view showing another example of the cleaning member for medical tubes of the present invention.

A cleaning member shown in FIG. 4 is shaped like a spherical body composed of fibers 5 having minute concavities and convexities formed thereon and an elastic core material 6, made of sponge or an elastic material, embedded in the center of the spherical body so that the cleaning member A4 holds an elastic force therein. In other words, the spherical cleaning member A4, the fibers 5 are mounted on the periphery of the elastic core material 6 in such a way that the former encloses the latter. Therefore the cleaning member A4 does not get out of shape, and the elasticity thereof is increased owing to the presence of the elastic core material 6. The cleaning member A4 moves together with the cleaning liquid in various directions while it is rotating at small angles in dependence on a degree of a resistance applied to the cleaning member from the surface of the duct of the endoscope against which the cleaning member is pressed. Thereby, after the endoscope is used, i.e., after examination terminates, the cleaning member A4 wipes and rubs the entire surface in the duct efficiently to thereby wipe off and rub off not only secretions such as mucus, blood, tissue pieces, but also viruses, bacteria, and pollutants such as various microbes that are difficult to remove from the surface of the duct of the endoscope, with them attaching to the inside of the surface-side fibers 5 having minute concavities and convexities. At this time, the cleaning liquid constantly flows inside the surface-side fibers 5 having minute concavities and convexities. Thus the cleaning member A4 wipes and rubs the pollutants that have attached to the fibers to thereby wipe off and rub off the pollutants, while the cleaning member A4 is washing off the pollutants into the cleaning liquid. Because the cleaning member A4 is highly elastic, it moves flexibly in the duct in conformity to different diameters (inner diameters) of ducts of endoscopes and stepped portions between adjacent parts of the duct having different diameters, and curves (angles). That is, it never occurs that the cleaning member A4 clogs in the duct and cannot be taken out therefrom. The cleaning member A4 moves while it is rotating at small angles owing to contact between it and the surface of the duct of the endoscope when it wipes and rubs the surface of the duct. That is, the cleaning member removes and cleans all the pollutants that have attached to the surface of the duct of the endoscope.

The diameter of each of the above-described spherical cleaning members is so set as to be a little larger than or equal to that of the duct of the endoscope. The spherical cleaning members are selectively used in conformity to the diameter, for example, 2.4 mm, 2.8 mm, and 3.4 mm of the duct of the endoscope. It is desirable that the cleaning members are flexible to such an extent that they can keep spherical when no pressure is applied thereto, are superior in wipe-off and rub-off performance, are deformable to such an extent that they are movable in conformity to different diameters of the duct of the endoscope and stepped portions between adjacent parts of the duct having different diameters, and curves (angles), have an elasticity having a restoring force, and are suitable for mass production. According to experimental results conducted in sufficient consideration of viscosities of pollutants, amounts of pollutants, a sucked amount of the cleaning liquid, and a sucking pressure, it is desirable to clean the duct by sucking the cleaning liquid intermittently at desired intervals when not less than two nor more than five cleaning members are used. There is a possibility that when it is used once, the cleaning member has a lower strength and a deformation. Thus to accomplish cleaning securely, it is normal to dispose it when it is used once.

Figure 17:
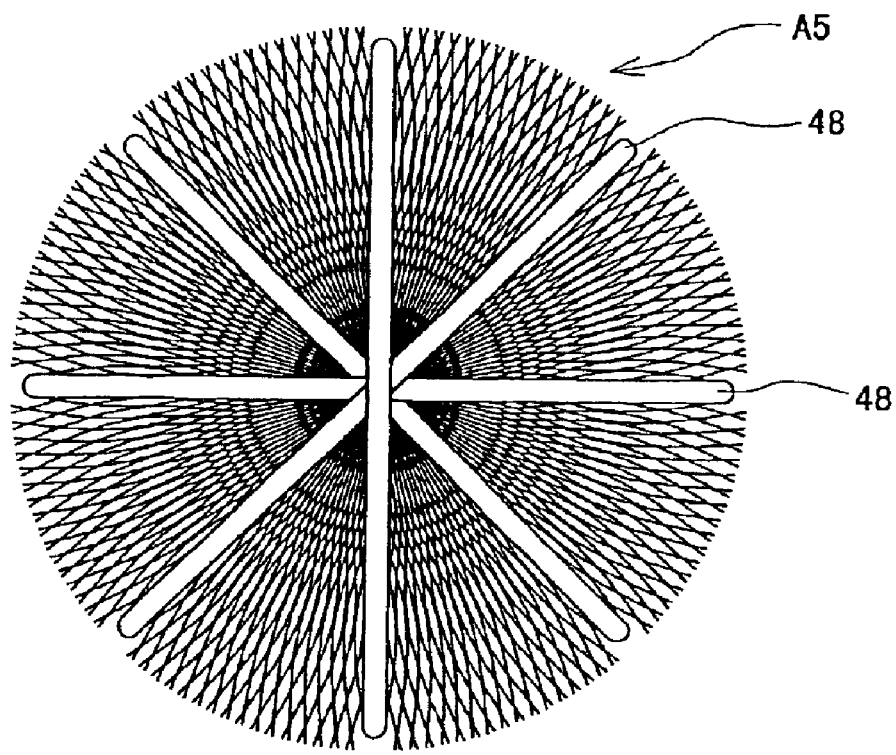
FIG. 17 is a schematic view showing an example of the cleaning member for medical tubes of the present invention.
Figure 18:
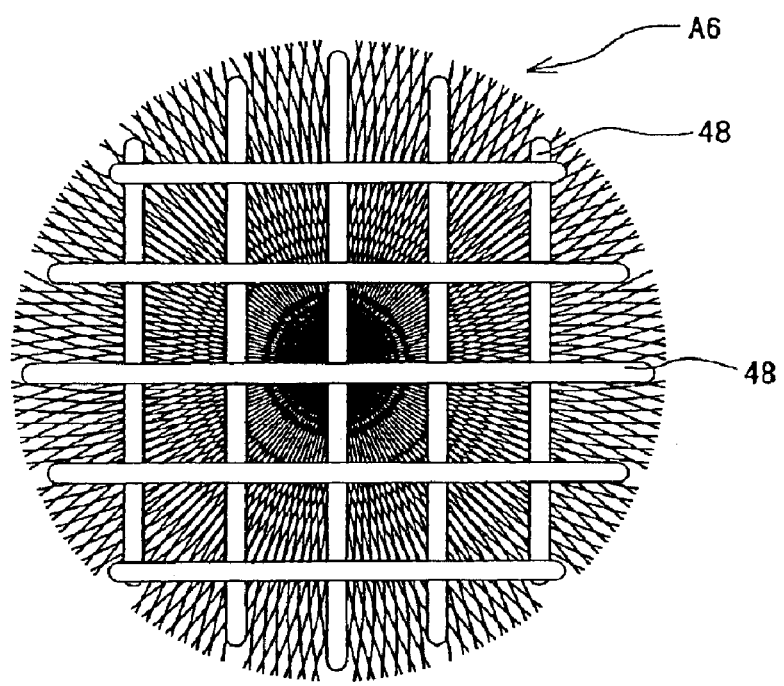
FIG. 18 is a schematic view showing another example of the cleaning member for medical tubes of the present invention.

As shown in FIG. 17, it is preferable that the cleaning member has one or a plurality of linear portions having a predetermined thickness on its outer surface. A cleaning member A5 has a plurality of linear portions 48. The cleaning member A5 can be rotated easily by providing it with the linear portions 48. The linear portion 48 is endless and continuous with the outer surface of the cleaning member A5 and has an intersection portion where all the linear portions 48 intersect with one another, as shown in FIG. 17. Therefore the linear portion 48 has a function of retaining the configuration of the cleaning member A5. The linear portion 48 having a configuration shown in FIG. 18 may be formed on the outer surface of a cleaning member A6. The linear portions 48 is so formed as to cover the outer surface of the cleaning member A6 in the shape of a lattice. The cleaning member A6 can be rotated easily by providing it with the linear portions 48. The linear portion 48 has a function of retaining the configuration of the cleaning member A6.

A porous member (above-described cleaning member) A1 of the present invention for cleaning a treatment appliance insertion lumen of an endoscope will be described below with reference to drawings.

The porous member A1 of the present invention for cleaning the treatment appliance insertion lumen of the endoscope is formed approximately spherically by molding a large number of superfine fibers. The porous member A1 can be swelled with an aqueous cleaning liquid. When the porous member A1 swells, the outer diameter of the porous member A1 becomes larger than the inner diameter of a treatment appliance insertion lumen 44 of an endoscope D to be cleaned. Further because the porous member A1 deforms, the porous member A1 can be inserted into the treatment appliance insertion lumen 44 of the endoscope D. Moreover, the aqueous cleaning liquid flowing into the treatment appliance insertion lumen 44 of the endoscope D allows the porous member A1 to move in contact with an inner wall of the lumen 44.

When the porous member is swelled with the cleaning liquid, the porous member deforms and the outer diameter thereof becomes larger than the inner diameter of the lumen to be cleaned. Thus the porous member can be inserted into the lumen. The porous member moves inside the lumen, with the porous member in close contact with the inner wall of the lumen. Therefore the porous member is capable of securely removing pollutants (secretion, bacteria, and the like) that have attached to the inner wall of the lumen. Since the porous member is deformable, it follows a change of the configuration of the lumen.

As the aqueous cleaning liquid, a cleaning liquid containing an agent of fat protein decomposition enzyme is usually used. The cleaning liquid contains water as its solvent. If necessary, the cleaning liquid contains a surface active agent.

The porous member A1, of the embodiment shown in FIG. 1, for cleaning the treatment appliance insertion lumen of the endoscope is approximately spherically formed by molding a large number of the superfine fibers, with the superfine fibers intertwined three-dimensionally. The porous member of the embodiment removes pollutants that have attached to the inner wall of the to-be-cleaned lumen by capturing them onto the surface thereof and into the inside thereof.

The porous member of the embodiment is formed approximately spherically by molding a large number of the superfine fibers intertwined three-dimensionally. The porous member has pores formed among fibers. Pores formed in the porous member do not extend linearly from a portion of one surface thereof to a portion of another surface thereof but formed as a disorderly aggregation thereof formed by partial connections of a large number of gaps formed among the fibers. As the fibers constituting the porous member, fibers hydrophilic to some extent are used. Therefore, when the porous member contacts the aqueous cleaning liquid, the aqueous cleaning liquid penetrates into the porous member and swells the porous member and makes the outer diameter thereof larger. The swelling of the porous member is not necessarily attributed to this structure. For example, it is possible to use fibers that absorbs the cleaning liquid and swell. It is also possible to use a porous member in which fibers themselves swell and structurally swell.

It is favorable that the superfine fibers for use in the porous member of the present invention is flexible and hydrophilic to some extent. It is more favorable that the superfine fibers for use in the porous member of the present invention is hydrophilic to some extent and hydrophobic to some extent. The porous member is capable of absorbing an aqueous liquid by means of a hydrophilic part of fibers thereof and sucking secretion which have attached to the inner wall of the lumen to a higher extent by means of a hydrophobic part of the fibers thereof. It is preferable that the fiber of the porous member is flat and superfine. The flat and superfine fiber adhere to the inner wall of the lumen to a higher extent and contacts the inner wall of the lumen in a larger area.

More specifically, it is preferable that the superfine fiber consists of an ethylene vinyl alcohol copolymer, a composition of the ethylene vinyl alcohol copolymer and other thermoplastic polymers or substances formed by partly crosslinking them. As the other thermoplastic polymers, it is possible to show polyester, polyamide, and polyolefin (for example, polypropylene, polyethylene). It is preferable that the composite fibers has a multi-layer structure of the ethylene vinyl alcohol copolymer and other thermoplastic polymers. As the multi-layer structure, it is possible to show core sheath type, eccentric core sheath type, multi-layer lamination type, side-by-side pattern, random composite type, radial lamination type, and superfine fiber division type. The composite fibers of the ethylene vinyl alcohol copolymer and other thermoplastic polymers have a high strength. As the superfine fibers to be used as the porous member of the present invention, multi-layer division type superfine fibers composed of the ethylene vinyl alcohol copolymer and polyethylene terephthalate can be preferably used. It is preferable that each superfine fiber has a sectional area of less than 10 $\mu m^2$.

It is preferable that like the porous member of this embodiment, the porous member has a core layer consisting of dense superfine fibers and an outer layer which covers the core layer and consists of superfine fibers not as dense as the superfine fibers of the core layer. This construction allows the porous member to be swelled easily by the aqueous cleaning liquid and easily capture the secretion which have attached to the inner wall of the lumen. It is appropriate that the size of the core layer is 10% to 70% of the diameter of the spherical porous member and that the size (thickness) of the outer layer is 15% to 45% of the diameter of the spherical porous member.

Although the size of the porous member is different according to the inner diameter of the lumen to be cleaned, it is suitable that the size of the porous member is 1 mm to 5 mm. It is suitable that the size of the porous member becomes larger than the inner diameter of the to-be-cleaned lumen owing to swelling thereof caused by contact between the porous member and the cleaning liquid. Thus the diameter of the porous member before it swells may be larger or smaller than the inner diameter of the to-be-cleaned lumen. It is preferable that the diameter of the porous member after it swells is 1.1 times to 1.5 times as large as the inner diameter of the lumen. Since the porous member is flexible and has a porous construction, the porous member is entirely deformable. Thus the porous member penetrates into the lumen, with the porous member deforming appropriately. The porous member may be moved by the cleaning liquid flowing in the lumen, while the porous member is rotating. In this case, it is preferable that the porous member rotates slowly.

As shown in FIG. 17, it is preferable that the porous member has one or a plurality of linear portions having a predetermined thickness on its outer surface. A porous member A5 has a plurality of linear portions 48. The porous member A5 can be rotated easily by providing it with the linear portions 48. The linear portion 48 is endless and continuous with the outer surface of the porous member A5 and has an intersection portion where all the linear portions 48 intersect with one another, as shown in FIG. 17. Therefore the linear portion 48 has a function of retaining the configuration of the porous member A5. The linear portion 48 having a configuration shown in FIG. 18 may be formed on the outer surface of a porous member A6. The linear portions 48 is so formed as to cover the outer surface of the porous member A6 in the shape of a lattice. The porous member A6 can be rotated easily by providing it with the linear portions 48. The linear portion 48 has a function of retaining the configuration of the porous member A6.

Any endoscope, having a treatment appliance insertion lumen, which can be inserted into the human body can be used in the present invention. Therefore both a hard endoscope and a soft endoscope can be used. The endoscope that can be used in the present invention includes an electronic endoscope, a digestive tract endoscope, a bronchia scope, an esophagoscope, a bile duct endoscope, an ultrasonic endoscope, a laparoscope, a rectum endoscope, a thracoscope, an arthroscope, a mediastinoscope, and a uteroscope.

Figure 13:
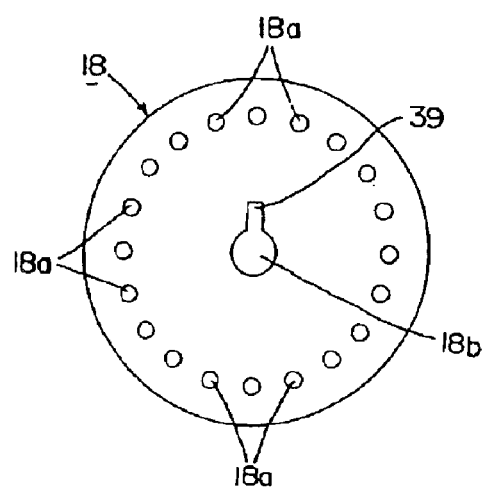
FIG. 13 is a side view showing an example of the cleaning member-holding plate.
Figure 14:
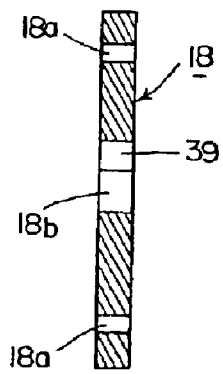
FIG. 14 is a sectional view showing the cleaning member-holding plate of FIG. 13.

A cleaning instrument of the present invention for cleaning a treatment appliance insertion lumen of an endoscope will be described below with reference to FIGS. 13 and 14.

The cleaning instrument of the present invention for cleaning the treatment appliance insertion lumen of the endoscope includes a cartridge body 18 having a plurality of through-holes 18a circumferentially disposed equiangularly or at equal intervals and porous members (not shown), for cleaning the treatment appliance insertion lumen of the endoscope, accommodated in a plurality of the through-holes 18a respectively.

The above-described porous member to be accommodated in a plurality of the through-holes 18a is used as the porous member for cleaning the treatment appliance insertion lumen of the endoscope.

In the cleaning instrument of the embodiment for cleaning the treatment appliance lumen, the cartridge body 18 has not less than two through-holes 18a formed equiangularly on the circumference of a circle. The porous member is accommodated in each of not less than two through-holes 18a. It is preferable that the cartridge body 18 has not less than three through-holes 18a and that the porous member is accommodated in each of not less than three through-holes 18a.

The cartridge body 18 of this embodiment has an opening 18b, at the center thereof, engaging a rotation shaft of a porous member-feeding instrument which will be described later. As described above, a large number of through-holes 18a is formed on the cartridge body 18. As shown in FIGS. 13 and 14, the cartridge body 18 is disk-shaped. The cartridge body 18 may be a polygonal plate. In this embodiment, the inner diameter of the through-hole 18a is constant from its one end to its other end. The porous member is accommodated in the through-hole 18a. The inner diameter of the through-hole 18a is a little smaller than the outer diameter of the porous member. Thus the porous member is accommodated in a deformed state in the through-hole 18a, with the porous member pressed against the inner surface of the through-hole 18a. Therefore the porous member is not removed from the through-hole 18a by a normal operation. A portion of the outer surface of the porous member in the vicinity of the through-hole 18a is smooth.

Figure 15:
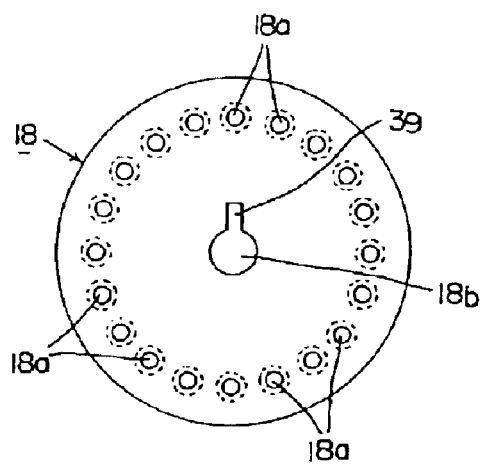
FIG. 15 is a side view showing another example of the cleaning member-holding plate.
Figure 16:
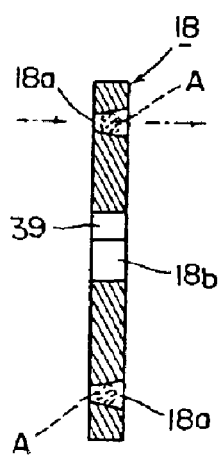
FIG. 16 is a sectional view showing the cleaning member-holding plate of FIG. 15.

The cartridge body 18 may be constructed as shown in FIGS. 15 and 16. The cartridge body of this embodiment is different from the above-described one in only the shape of the through-hole 18a. In this embodiment, the inner diameter of the through-hole 18a at one end thereof is smaller than the outer diameter of the porous member to be accommodated therein, and the inner diameter of the through-hole 18a at the other end thereof is larger than the inner diameter thereof at the one end thereof. As shown clearly in FIG. 16, the through-hole 18a is so formed that the inner diameter thereof increases gradually from one end thereof to the other end thereof. This construction facilitates the removal of the porous member from the through-hole 18a, when the cleaning liquid flows in the cartridge body. The configuration of the through-hole 18a is not restricted to the above-described tapered one. For example, the through-hole 18a may be so formed that the diameter at its one end is small and the diameter at its other end is large. As another example, the inner diameter of the through-hole 18a may become larger stepwise from its one end toward its other end. It is preferable to set the inner diameter of the through-hole 18a at its other end a little larger than the outer diameter of the porous member to be accommodated therein. This construction facilitates an insertion of the porous member into the through-hole 18a. A liquid may be filled into the through-hole 18a, together with the porous member. As the liquid to be filled into the through-hole 18a, sterile water (for example, distilled water, RO water), a physiological saline solution, and a cleaning liquid for lumen, and disinfectant-containing water are conceivable.

The cartridge body is not limited to the above-described one in its construction, but may have through-holes arranged linearly at regular intervals.

A hard resin and a semirigid resin are suitable as materials for the cartridge body. More specifically, it is possible to use polycarbonate, acrylic resin, polyester (fox example, polyethylene terephthalate, polybutylene terephthalate), polyolefin (for example, polyethylene, polypropylene, ethylene-propylene copolymer), styrene resin (polystyrene, MS resin (methacrylate-styrene copolymer), polyvinyl chloride (hard vinyl chloride), and polyamide (nylon 6, nylon 66).

A cleaning apparatus of the present invention for cleaning a treatment appliance insertion lumen of an endoscope will be described below with reference to FIGS. 5 through 16.

The cleaning apparatus of the present invention for cleaning the treatment appliance insertion lumen of the endoscope includes a cleaning instrument, for cleaning the treatment appliance insertion lumen of the endoscope, having a cartridge body 18 provided with a plurality of through-holes 18a disposed equiangularly or at regular intervals and porous members accommodated in the through-holes 18a respectively; and a feeding instrument, for feeding the lumen-cleaning porous members, having a cleaning instrument accommodation portion removably accommodating the cleaning instrument, a cleaning liquid inflow side guide path 24 communicating with one end of one through-hole 18a of the cartridge body 18 of the cleaning instrument accommodated in the cleaning instrument accommodation portion, a cleaning liquid outflow side guide path 25 communicating with the other end of the through-hole 18a, an endoscope-end mounting portion 20 disposed at an end of the cleaning liquid outflow side guide path 25, and a cartridge-driving mechanism for operating the cartridge body 18 in such a way that each through-hole 18a of the cartridge body 18 communicates with the cleaning liquid inflow side guide path 24 and the cleaning liquid outflow side guide path 25.

The cleaning apparatus for cleaning the treatment appliance insertion lumen of the endoscope includes the cleaning instrument for cleaning the treatment appliance insertion lumen of the endoscope and the feeding instrument for feeding the lumen-cleaning porous member accommodated in the feeding instrument into the treatment appliance insertion lumen.

The above-described cleaning instrument for cleaning the treatment appliance insertion lumen of the endoscope and the above-described lumen-cleaning porous member to be accommodated in the feeding instrument are used in the present invention.

The feeding instrument of the present invention for feeding the lumen-cleaning porous member will be described below with reference to FIGS. 5 through 16.

The feeding instrument of the present invention for feeding the lumen-cleaning porous member has the cleaning instrument accommodation portion accommodating the feeding instrument, the cleaning liquid inflow side guide path 24 communicating with one end of one through-hole 18a of the cartridge body 18 of the cleaning instrument accommodated in the cleaning instrument accommodation portion, the cleaning liquid outflow side guide path 25 communicating with the other end of the through-hole 18a, the endoscope-end mounting portion 20 disposed at the end of the cleaning liquid outflow side guide path 25, and the cartridge-driving mechanism for operating the cartridge body 18 in such a way that each through-hole 18a of the cartridge body 18 communicates with the cleaning liquid inflow side guide path 24 and the cleaning liquid outflow side guide path 25.

The feeding instrument for feeding the lumen-cleaning porous member has a function of feeding the lumen-cleaning porous members accommodated in the through-holes of the cleaning instrument into the to-be-cleaned lumen of the endoscope one by one.

The feeding instrument of the embodiment for feeding the cleaning instrument has a body B and a cover C. The cleaning instrument accommodation portion is formed between the body B and the cover C. The entire feeding instrument of the embodiment is pistol-shaped. A shaft 7 supports the cover C pivotally on the body B. The cover C is longitudinally pivotal at a predetermined angle (preferably not less than 90 degrees) around the shaft 7. In other words, the cover C can be opened and closed. The cover C is not limited to such a type, but may be removable from the body B.

The cover C has a function of closing the body B accommodating the cleaning instrument. The cover C is provided with the cleaning liquid inflow side guide path 24 communicating with the one end of the through-hole of the cleaning instrument (cartridge body) accommodated in the body B. The inner diameter of the cleaning liquid inflow side guide path 24 at the one end of the through-hole is set a little larger than the inner diameter of the through-hole at its one end. A cleaning liquid suction pipe 8 is connected to a connection port 9 of the cleaning liquid inflow side guide path 24.

In this embodiment, the cover C has a mounted state-holding member for keeping the cover C installed on the body B. More specifically, the cover C has an engaging member 10 having a convexity 10a, disposed at its tip, engaging the body B when the cleaning instrument accommodation portion is opened and closed. In this embodiment, the engaging member 10 is leaf spring-shaped. The leaf spring-shaped engaging member 10 is fixed to the cover C with a fastening screw 11. An O-ring 14 for making the gap between an end surface 12 of the cover C and a front end surface 13 of the body B substantially liquid-tight is provided on an inner end surface of the cover C. The mounted state-holding member of the cover C for keeping the cover C installed on the body B is not limited to the above-described type. For example, a screw hole may be formed on one of the cover C and the body B, and a screw engaging the screw hole may be provided on the other. As another example, a magnet may be provided on the cover C and/or the body B to keep the cover C and the body B installed on each other by a magnetic force.

The body B has the cleaning instrument accommodation portion.

On the front end surface 13 of the connection portion of the body B which is connected to the cover C, the body B has an accommodation portion (concavity) 22 for removably accommodating the cleaning instrument (cartridge body) 18 therein. An urging means 23 for urging the cleaning instrument accommodated in the accommodation portion 22 in a direction away from the accommodation portion 22 is provided on a surface of the body B which contacts the cleaning instrument accommodated in the accommodation portion 22. Several elastic members 23 for pressing out the cartridge body 18 from the accommodation portion 22 by a predetermined dimension (20% to 80% of thickness of cartridge body 18) is used as the urging means. A coil spring is used as the elastic member 23. Rubber or elastomer may be used as the elastic member 23. A plurality of the elastic members 23 is disposed on the circumference of a circle. The urging means facilitates removal of the cleaning instrument from the accommodation portion 22. The mounted state-holding member of the cover C for keeping the cover C installed on the body B holds the cover C so that the cover C is not removed from the body B by the urging force of the urging means.

The body B has the cleaning liquid inflow side guide path 24 communicating with the other end of the through-hole of the cleaning instrument (cartridge body) accommodated in the accommodation portion. The endoscope-end mounting portion 20 is provided at a connection port of the cleaning liquid outflow side guide path 25. The endoscope-end mounting portion 20 has a connection pipe 20a and a connector 20b. The connection pipe 20a of the endoscope-end mounting portion 20 is fixed to the body B in such a way that the connection pipe 20a communicates with the cleaning, liquid outflow side guide path 25. The connector 20b is fixed to a rear end of the connection pipe 20a. The connection pipe and the connector may be integral with each other.

Figure 5:
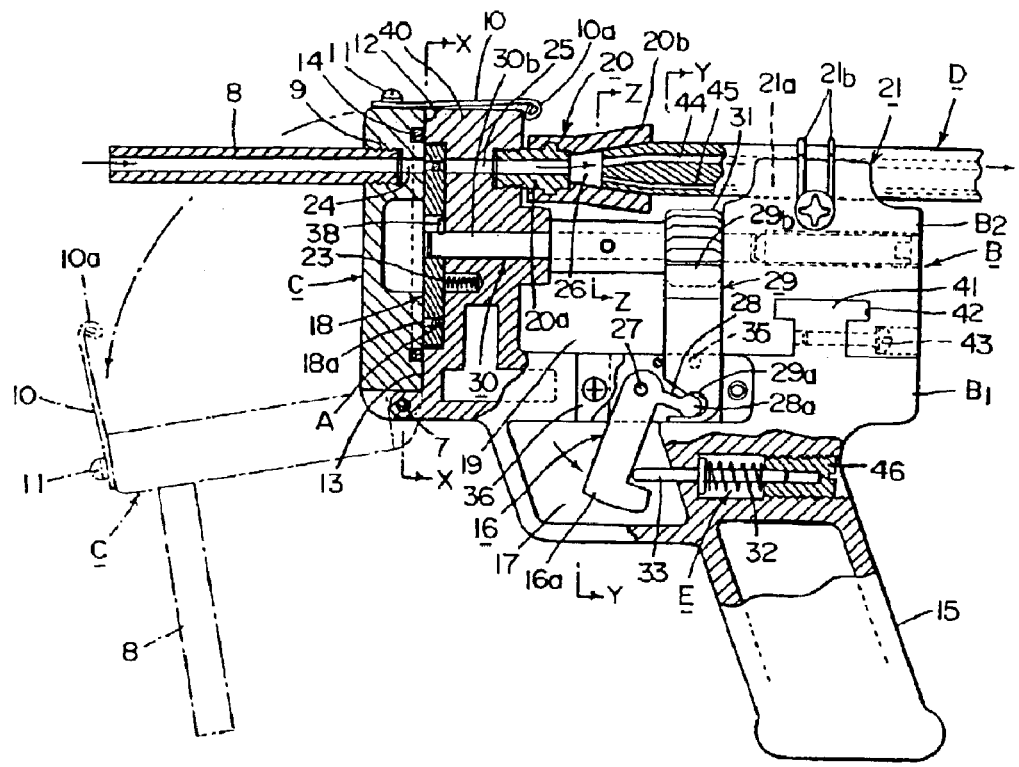
FIG. 5 is a partly cut side view showing an example of a porous member-feeding instrument for medical tubes of the present invention.
Figure 6:
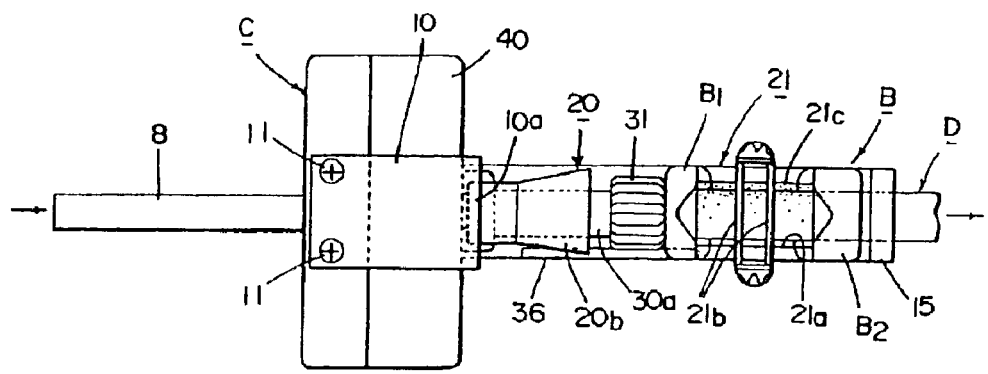
FIG. 6 is a plan view showing the porous member-feeding instrument of FIG. 5.
Figure 7:
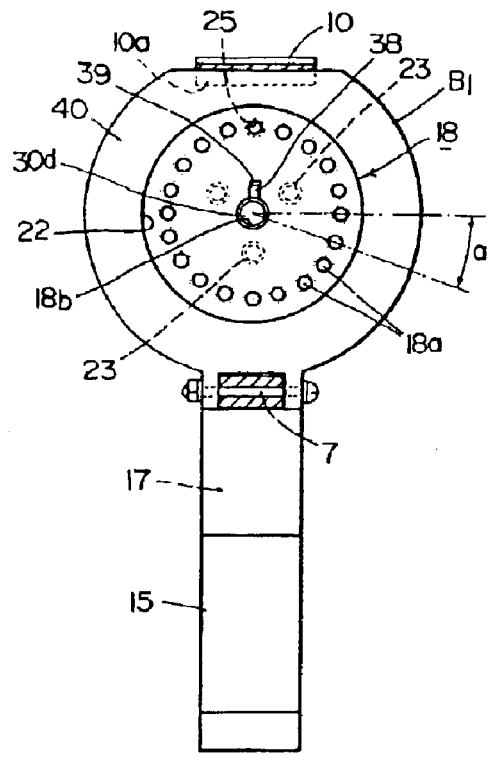
FIG. 7 is a side view taken along a line X—X of FIG. 5.
Figure 8:
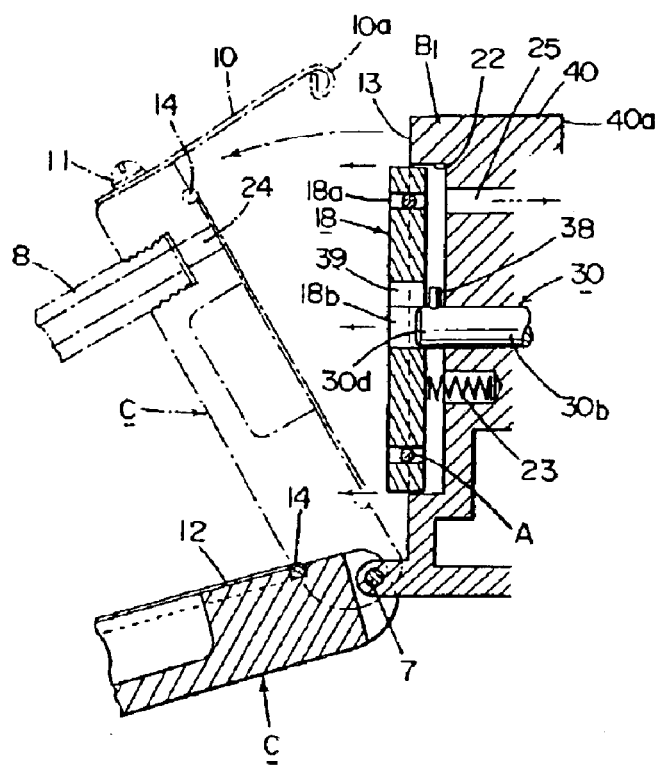
FIG. 8 is an enlarged sectional view showing a fit-in portion of a cleaning member-holding plate.

It is preferable that in the state where the end of the endoscope is mounted on the endoscope-end mounting portion 20, the endoscope-end mounting portion 20 has a guide space 26 for guiding the lumen-cleaning porous member A to the treatment appliance insertion lumen 44. The guide space 26 is formed between an end of an endoscope D and the inner surface of the endoscope-end mounting portion 20 in such a way that the inner diameter of the guide space 26 is larger than that of the cleaning liquid outflow side guide path 25 and the lumen 44. As shown in FIG. 5, the guide space 26 is formed inside the connector 20b. The guide space 26 may be formed inside the connector pipe.

It is preferable that the base side (connector) of the endoscope-end mounting portion 20 is formed of an elastic or flexible material to mount the end of the endoscope (normally, tip of endoscope) on the endoscope-end mounting portion 20 easily and substantially liquid-tightly. As shown in FIG. 5, it is preferable that the diameter of the base side (connector) of the endoscope-end mounting portion 20 increases toward an end (open end) thereof. This construction facilitates the connection between the endoscope-end mounting portion 20 and endoscopes having different outer diameters. Between the connection pipe 20a and the endoscope, the guide space 26 is formed to guide the porous member into the lumen of the endoscope when the endoscope-end mounting portion 20 is connected to the endoscope. It is preferable that the distance of the guide space 26, namely, the distance between the tip of the tube D inserted into the endoscope-end mounting portion 20 and the end surface of the connection pipe 20a is long enough to smoothly guide the lumen-cleaning porous member into the lumen of the endoscope.

Normally, the connection pipe and the lumen of the endoscope are not disposed linearly. Therefore by forming the guide space 26 as described above, the lumen-cleaning porous member which has flowed out from the connection pipe flows smoothly toward the lumen.

As the material for forming the base side (connector) of the endoscope end mounting portion 20, the following substances can be used: urethane rubber, silicone rubber, synthetic rubber such as butadiene rubber, natural rubber such as latex rubber, soft vinyl chloride, olefin elastomer (polyethylene elastomer, polypropylene elastomer), styrene elastomer (for example, styrene-butadiene-styrene copolymer, styrene-isoprene-styrene copolymer, styrene-ethylene butylene-styrene copolymer), polyurethane, urethane elastomer. Thermoplastic polyurethane is particularly preferable. It is preferable that these materials are transparent. The transparent materials allow an operator to check a flow situation of the lumen-cleaning porous member into the lumen. A sealing annular rib (not shown) may be provided on the inner surface of the connector.

The guide space facilitates guide of the lumen-cleaning porous member into the to-be-cleaned lumen and functions as a liquid reserving portion. Owing to the formation of the guide space, the lumen-cleaning porous member floatingly stays temporarily therein in only a very short period of time during which the lumen-cleaning porous member passes therethrough together with the cleaning liquid, swells, and is sucked smoothly and guided into the lumen together with the cleaning liquid owing to a sucking action. Thereby the lumen can be cleaned. Further the lumen-cleaning porous member securely contacts the cleaning liquid filled into the guide space 26. Thus the lumen-cleaning porous member swells reliably. Thereby the lumen-cleaning porous member is prevented from flowing into the lumen, with the lumen-cleaning porous member compressed inside the through-hole of the cartridge body, thus cleaning the inner wall of the lumen securely.

In this embodiment, the connector 20b is removable from the connection pipe 20a. Thus only the connector 20b can be cleaned.

As described above with reference to FIGS. 15 and 16, the cleaning instrument may have the through-hole whose inner diameter at one side is smaller than the outer diameter of the porous member and whose inner diameter at the other side is larger than the inner diameter at the one side. In this case, it is preferable that the cleaning instrument accommodation portion 22 of the body B is capable of accommodating the cleaning instrument in such a way that the other side (larger-diameter side) of the through-hole of the cleaning instrument is disposed at the side of the cleaning liquid outflow side guide path 25. Thereby it is possible to prevent erroneous mounting of the cleaning instrument. A projected portion (or annular concavity) is formed on the surface, of the cleaning instrument accommodation portion 22 of the body B, at which the cleaning instrument accommodation portion 22 and the cleaning member contact each other. Further an annular concavity (or projected portion) for accommodating the projected portion of the projected portion of the cleaning instrument accommodation portion 22 is formed on the surface, of the cartridge body, at which the cleaning instrument accommodation portion and the cartridge body contact each other.

The feeding instrument for feeding the lumen-cleaning porous member has the cartridge-driving mechanism for operating the cartridge body 18 so that the through-holes 18a of the cartridge body 18 communicate with the cleaning liquid inflow side guide path 24 and the cleaning liquid outflow side guide path 25.

The feeding instrument of this embodiment has a grip 15, the driving mechanism for rotating the cleaning instrument (cartridge body) 18, and an operation lever 16 for operating the driving mechanism.

As shown in FIG. 5, the feeding instrument of this embodiment is pistol-shaped. The cleaning liquid suction pipe 8 of the cover C corresponds to the muzzle of a pistol. The operation lever 16 corresponds to the trigger of the pistol. The cleaning instrument and the cleaning instrument accommodation portion correspond to the magazine of the pistol. The feeding instrument has a holding portion 21 for holding the base side of the endoscope D by a predetermined distance from the tip of the endoscope D. The holding portion 21 has a semicircular concavity 21a and an elastic string member 21b. A cushioning plate member 21c is laid on the semicircular concavity 21a.

A hard resin, a semirigid resin, and metal are suitable as materials for the cover and the body of the feeding instrument. More specifically, it is possible to use polycarbonate, acrylic resin, polyester (fox example, polyethylene terephthalate, polybutylene terephthalate), polyolefin (for example, polyethylene, polypropylene, ethylene-propylene copolymer), styrene resin (polystyrene, MS resin (methacrylate-styrene copolymer), polyvinyl chloride (hard vinyl chloride), and polyamide (nylon 6, nylon 66). As metal, stainless steel and aluminum alloy can be suitably used.

The body B of the feeding instrument is composed of a main member (main body) B1 having the grip 15, and a space 17, and a tip-mounting portion 40 integral with one another and a rear end-mounting member B2 removably mounted on the rear portion of the main member B1. The rear end-mounting member B2 can be connected to the main member B1 by sliding the rear end-mounting member B2 on the main member B1 through a convexity 41 of the main member B1 and a concavity 42 of the rear end-mounting member B2. The main member B1 and the rear end-mounting member B2 are fixed to each other with a fastening bolt 43. The endoscope D accommodates the treatment appliance insertion lumen 44 and a duct 45 for feeding air and water.

Figure 9:
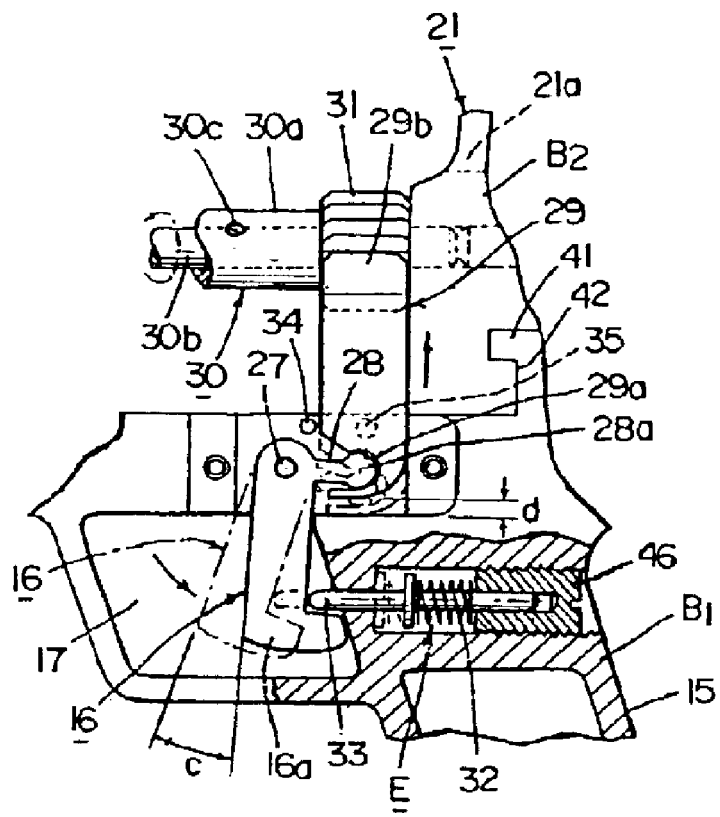
FIG. 9 is a side view showing a rotation transmission mechanism when it rotates.
Figure 10:
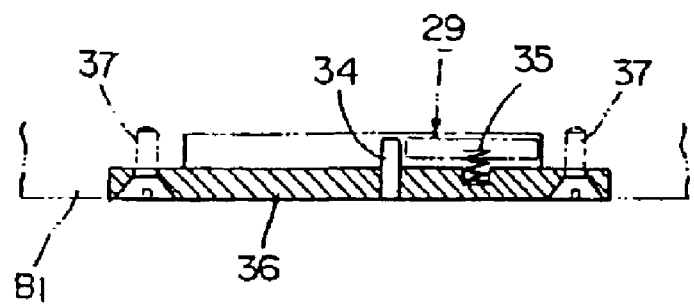
FIG. 10 is a sectional view showing a pressing plate.
Figure 11:
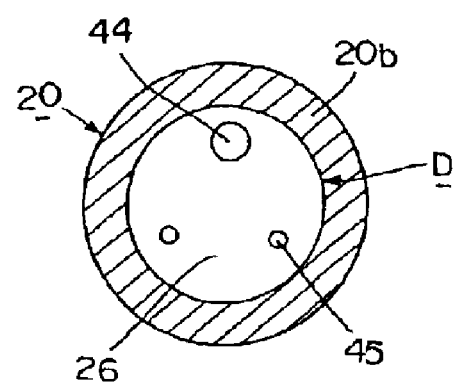
FIG. 11 is a sectional view, showing an insertion portion, taken along a line Z—Z line of FIG. 5
Figure 12:
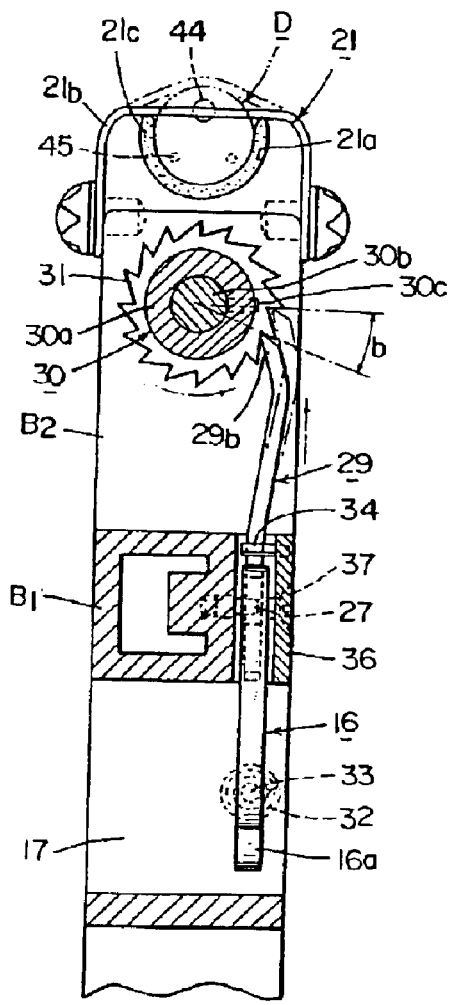
FIG. 12 is a sectional view taken along a line Y—Y of FIG. 5.

The cartridge-driving mechanism of the feeding instrument of this embodiment drives the cartridge body 18 stepwise at an angle between the adjacent through-holes 18a or at an interval between the adjacent through-holes 18a. More specifically, as shown in FIGS. 5, 9, and 12, the feeding instrument has the operation lever 16 that is supported by a shaft 27 in such a way that the operation lever 16 pivots in a right-to-left direction (see FIGS. 5 and 9) on the shaft 27. The operation lever 16 has an operation arm 28 extending from one end of the operation lever 16 in a direction perpendicular to the operation lever 16. A tip engagement convexity 28a of the operation arm 28 is moved upward by pulling the operation lever 16. The tip engagement convexity 28a of the operation arm 28 is in engagement with an engaging concavity 29a disposed at a lower end of a claw plate 29 vertically movable. Thus when the tip engagement convexity 28a of the operation arm 28 is driven upward, the claw plate 29 moves upward. The feeding instrument has a rotation shaft 30. A ratchet gear 31 is fixed to the rear end of the rotation shaft 30. An end of the claw plate 29 is in engagement with a tooth of the ratchet gear 31. The ratchet gear 31 is rotated by an upward movement of the claw plate 29. The feeding instrument has an automatic return means E for urging the operation lever 16 in a direction in which the operation lever 16 returns to its original position.

When the operation lever 16 is pulled by a given stroke c toward an operator against the urging force of the automatic return means E, the operation arm 28 moves the claw plate 29 upward by a given stroke d (see FIGS. 9 and 12). The claw plate 29 which has moved upward rotates the ratchet gear 31 by one tooth (predetermined angle) b. Thus the rotation shaft 30 rotates by one tooth of the ratchet gear 31. The rotation shaft 30 has a cylindrical shaft 30a and a central shaft 30b. Both are fixed to each other with a fastening screw 30C.

The automatic return means E has a return pin 33 that contacts the operation lever 16 and a return spring 32 for pressing the return pin 33 to the left in FIGS. 5 and 9. More specifically, the return pin 33 presses the inner side of the lower end of a lower operation portion 16a of the operation lever 16 to always urge the operation lever 16 in a direction in which the operation lever 16 is placed in an unoperative state (state shown in FIG. 5). Therefore the claw plate 29 interlocked to the operation lever 16 is urged in such a way that the claw plate 29 is placed in an unoperative state (state shown in FIG. 5, state in which the claw plate 29 does not move upward). Therefore when the operation of pulling the operation lever 16 is released, the automatic return means E returns the operation lever 16 and the claw plate 29 automatically to the original position respectively, and a tooth of the ratchet gear 31 below the tooth thereof in engagement with the ratchet gear 31 rides across an upper-end claw portion 29b of the claw plate 29 and engages the upper-end claw portion 29b, thus preparing for a subsequent rotation operation. The force of the return spring 32 can be adjusted by a receiving member 46. The claw plate 29 moves vertically without moving laterally because a guide pin 34 guides the claw plate 29. A pressing spring 35 presses the claw plate 29 against the ratchet gear 31 to allow the upper-end claw portion 29b of the claw plate 29 to engage the ratchet gear 31 tooth by tooth sequentially and securely. A pressing plate 36 holds the operation lever 16 and the claw plate 29 so that the upper part of the operation lever 16 and the lower part of the claw plate 29 are not disconnected from each other. The pressing plate 36 and the return spring 32 hold the claw plate 29 so that the claw plate 29 does not fall sideways. The pressing plate 36 has the guide pin 34 and the pressing spring 35 (see FIG. 10). Both ends of the pressing plate 36 are fixed to the body B of the feeding instrument with a fastening screw 37.

The cleaning instrument (cartridge body) 18 to be used for the cleaning apparatus of this embodiment has a plurality of cleaning instrument-holding through-holes 18a formed on the circumference of a circle equiangularly. The rotation angle b of one tooth of the ratchet gear 31 is set equally to the angle formed between the adjacent through-holes 18a formed on the cartridge body 18. The cartridge body has a rotation shaft-installing hole 18b formed at the center of the circumference. The leading end (leading end of the center shaft 30b) of the rotation shaft 30 is capable of penetrating into the installing hole 18b. A rotation transmission function for transmitting the rotation of the rotation shaft 30 to the cartridge body 18 is provided on the installing hole 18b and the leading end of the rotation shaft 30. More specifically, the rotation shaft 30 has a projected portion (engaging pin) 38 projected outward from the peripheral surface of the leading end 30d thereof. The installing hole 18b of the cartridge body 18 is provided with an engaging concavity 39 accommodating or engaging the engaging pin 38. Thus when the operation lever 16 is operated, the cartridge body 18 rotates intermittently, and adjacent through-holes communicate with the cleaning liquid inflow side guide path 24 and the cleaning liquid outflow side guide path 25. The cartridge body 18 is axially freely movable for the leading end 30d of the rotation shaft 30. Thus the cartridge body 18 does not prevent an operation of taking out the cleaning instrument from the cleaning instrument accommodation portion 22.

The operation of the cleaning apparatus of the present invention will be described below with reference to the above-described embodiments.

Initially, the cover C is opened to mount the cleaning instrument holding the lumen-cleaning porous member on the cleaning instrument accommodation portion 22 of the body B. More specifically, the cleaning instrument is installed on the cleaning instrument accommodation portion 22 in such a way that the position of the engaging concavity 39 of the installing hole 18b of the cartridge body 18 is coincident with that of the engaging pin 38 projected from the leading end 30d of the rotation shaft 30. Thereafter the cover C is closed and the convexity 10a disposed at the leading end of the engaging member 10 is engaged by a corner 40a of the tip-mounting portion 40 of the body B to thereby fix the cover C to the body B in a closed state. When the cover C is closed, the cleaning instrument (cartridge body) 18 compresses the spring 23 through the end surface 12 of the cover C, and the cleaning instrument 18 is rotatably accommodated in the accommodation portion 22 owing to the rotation of the rotation shaft 30. In this state, one through-hole 18a of the cartridge body 18 communicates linearly with the cleaning liquid inflow side guide path 24 and the cleaning liquid outflow side guide path 25 (see FIG. 5).

The feeding instrument of the embodiment uses the cartridge body having a plurality of the through-holes disposed circumferentially and the cleaning instrument having a plurality of lumen-cleaning porous members accommodated in the through-holes. The cleaning instrument may have through-holes linearly at regular intervals. In this case, the feeding instrument is not rotated, together with the cleaning member but is movable linearly at regular intervals.

Instead of the above-described manual type, the feeding instrument may be of a type of rotating the rotation shaft by a motor or the like.

After the use of the endoscope D finishes, i.e., after examination finishes, the cleaning apparatus is mounted on the endoscope, with the leading end of the endoscope D mounted on the endoscope-end mounting portion 20 and with the leading end of the endoscope D held at the holding portion 21. The leading end of the cleaning liquid suction pipe 8 connected with the connection port 9 of the cover C is immersed in a cleaning liquid bath (not shown) or a cleaning liquid supply pipe (not shown) is connected to the leading end of the cleaning liquid suction pipe 8. A cleaning liquid suction device (not shown) is mounted on the rear end of the endoscope. When the cleaning liquid suction device is operated, the cleaning liquid flows from the cleaning liquid suction pipe 8 into the lumen of the to-be-cleaned endoscope D through the cleaning liquid inflow side guide path 24 of the cover C, the through-hole 18a of the cartridge body 18, the cleaning liquid outflow side guide path 25 of the body of the feeding instrument, and the endoscope-end mounting portion (guide space). The lumen-cleaning porous member accommodated in the through-hole 18a is pressed by the cleaning liquid and flows into the guide space inside the endoscope-end mounting portion 20 through the cleaning liquid outflow side guide path 25, thus contacting the cleaning liquid inside the guide space. As a result, the porous member swells. Thus the diameter of the porous member becomes larger than the inner diameter of the to-be-cleaned lumen. Thereafter the porous member elongates longitudinally, thus flowing into the lumen 44. Thereafter the porous member which has flowed into the lumen 44 flows toward the rear end of the endoscope together with the cleaning liquid, with the porous member in close contact with the inner wall of the lumen 44 and rotating at small angles. While the porous member is moving in contact with the inner wall of the lumen 44, the porous member captures and removes body fluids, blood, secretions, tissue pieces, viruses, and microbes such as bacteria that have attached to the inner wall of the lumen.

When the operation lever 16 of the cleaning apparatus is manually pulled once, the claw plate 29 rotates the ratchet gear 31. Thus the rotation shaft 30 rotates at a predetermined angle through the ratchet gear 31. Owing to the rotation of the rotation shaft 30, the cartridge body 18 rotates at the angle formed between the adjacent through-holes 18a of the cartridge body 18. As a result, the porous member accommodated in the subsequent through-hole is pressed by the cleaning liquid and discharged from the cleaning instrument. Thereafter as in the case of the above-described porous member, the porous member flows into the guide space inside the endoscope-end mounting portion 20 through the cleaning liquid outflow side guide path 25 and then into the lumen 44. Thus when the operation lever 16 is pulled twice with an arbitrary time lag, three lumen-cleaning porous members can be supplied to the lumen.

In the lumen-cleaning porous member-feeding instrument of this embodiment, the cleaning member is of a cartridge type. Therefore the lumen-cleaning porous member-feeding instrument can be successively used by merely replacing the cleaning member. The cleaning member is automatically pressed out of the accommodation portion (fit-in concavity) 22 by a predetermined dimension when the cover C is opened. That is, when the cover C is opened, the cleaning member projects automatically from the accommodation portion 22 by the predetermined dimension. Thus the cleaning member can be easily removed from the accommodation portion 22.

Since the entire feeding instrument of this embodiment is pistol-shaped, it can be operated by holding it with one hand and can be formed compactly and lightly.

The present invention is not limited to the above-described embodiments but various modification can be made without departing from the spirit and scope thereof.

EXAMPLES

Multi-layer division-type superfine short fibers (sectional area: 10 $\mu m^2$) were composed of an ethylene vinyl alcohol copolymer and polyethylene terephthalate. The short fibers were rounded for granulation to prepare the cleaning member (porous member: outer diameter was about 2.5 mm) of the present invention.

Experiments of cleaning the clamp channel of an endoscope were conducted by using the spherical cleaning member of the present invention. As a result, data described below were obtained.

Using an electronic scope used in an examination of the upper digestive tract with an endoscope, 20 cc of a sterilized physiological saline solution was sucked to one end of a treatment appliance insertion lumen of the electronic scope, immediately after the examination finished. The physiological saline solution which flowed out from the other end of the lumen was collected in a sterilized spit. Using the collected physiological saline solution, the kind and amount of bacteria inside the clamp channel were examined before the lumen was cleaned. Thereafter the cleaning member of the above-described embodiment and 20 cc of the sterilized physiological saline solution were sucked to the electronic scope from one end thereof and discharged from the other end thereof to clean the inner wall of the lumen. Then 3 cc of the sterilized physiological saline solution was injected three times into the other side of the lumen. Thereafter the sterilized physiological saline solution was discharged from the one end of the lumen and collected in the sterilized spit.

The collected physiological saline solution was cultured. The result was as shown in table 1 to table.

TABLE 1

Result of culturing after upper digestive tract was examined with endoscope (seven cases)

| Case No. | Kind of bacteria | Culturing immediately after examination | Culturing after 20 cc of physiological saline solution was sucked |
|---|---|---|---|
| 1 | α-streptcoccus | $6 \times 10^7$ | $1 \times 10^4$ |
|   | Neisserria sp | $6 \times 10^7$ | $1 \times 10^4$ |
| 2 | α-streptcoccus | $2 \times 10^5$ | $1 \times 10^4$ |
|   | γ-streptcoccus | $1 \times 10^5$ | Below detection limit |
|   | Neisserria sp | $1 \times 10^5$ | Below detection limit |
| 3 | α-streptcoccus | $6 \times 10^7$ | $1 \times 10^4$ |
|   | γ-streptcoccus | $1 \times 10^7$ | Below detection limit |
|   | Neisserria sp | $4 \times 10^7$ | $1 \times 10^4$ |
| 4 | α-streptcoccus | $1 \times 10^7$ | $2 \times 10^4$ |
|   | Escherichia coli | $4 \times 10^7$ | $2 \times 10^5$ |
| 5 | α-streptcoccus | $1 \times 10^5$ | $4 \times 10^4$ |
|   | γ-streptcoccus | $2 \times 10^4$ | $2 \times 10^4$ |
| 6 | α-streptcoccus | $1 \times 10^7$ | $2 \times 10^4$ |
|   | Neisserria sp | $1 \times 10^6$ | $2 \times 10^4$ |
| 7 | α-streptcoccus | $6 \times 10^7$ | Below detection limit |
|   | γ-streptcoccus | $4 \times 10^7$ | Below detection limit |
|   | Neisserria sp | $4 \times 10^7$ | Below detection limit |
|   | Prevotella molaninogenica | $1 \times 10^5$ | $1 \times 10^5$ |

TABLE 2

Result of culturing after spherical cleaning member was used to clean endoscope used to examine upper digestive tract (16 cases)

| Case No. | Kind of bacteria | Culturing immediately after examination | Culturing after endoscope was cleaned by sucking one spherical cleaning member with 20 cc of physiological saline solution |
|---|---|---|---|
| 1 | α-streptcoccus | $4 \times 10^7$ | Below detection limit |
|   | γ-streptcoccus | $2 \times 10^7$ | Below detection limit |
|   | Neisserria sp | $2 \times 10^7$ | Below detection limit |
| 2 | α-streptcoccus | $6 \times 10^7$ | Below detection limit |
|   | γ-streptcoccus | $4 \times 10^7$ | Below detection limit |
|   | Neisserria sp | $4 \times 10^7$ | Below detection liniit |
|   | Klebsiella pneumoniae | $1 \times 10^7$ | Below detection limit |
| 3 | α-streptcoccus | $4 \times 10^7$ | Below detection limit |
|   | Neisserria sp | $6 \times 10^7$ | Below detection limit |
| 4 | α-streptcoccus | $6 \times 10^7$ | Below detection limit |
|   | γ-streptcoccus | $1 \times 10^7$ | Below detection limit |
|   | Neisserria sp | $1 \times 10^7$ | Below detection limit |
|   | Klebsiella pneumoniae | $1 \times 10^5$ | Below detection limit |
| 5 | α-streptcoccus | $1 \times 10^6$ | Below detection limit |
|   | Neisserria sp | $2 \times 10^7$ | Below detection limit |
|   | Klebsiella pneumoniae | $1 \times 10^4$ | Below detection limit |
| 6 | α-streptcoccus | $1 \times 10^4$ | Below detection limit |
|   | Neisserria sp | $1 \times 10^5$ | Below detection limit |
| 7 | γ-streptcoccus | $4 \times 10^4$ | Below detection limit |
|   | Neisserria sp | $4 \times 10^4$ | Below detection limit |
| 8 | α-streptcoccus | $6 \times 10^7$ | Below detection limit |
|   | γ-streptcoccus | $2 \times 10^7$ | Below detection limit |
|   | Neisserria sp | $5 \times 10^7$ | Below detection limit |
|   | Klebsiella pneumoniae | $1 \times 10^7$ | Below detection limit |
| 9 | α-streptcoccus | $2 \times 10^6$ | Below detection limit |
|   | Neisserria sp | $1 \times 10^7$ | Below detection limit |
|   | Klebsiella pneumoniae | $1 \times 10^6$ | Below detection limit |
| 10 | α-streptcoccus | $1 \times 10^7$ | Below detection limit |
|    | Neisserria sp | $1 \times 10^5$ | Below detection limit |
| 11 | γ-streptcoccus | $1 \times 10^5$ | Below detection limit |
| 12 | α-streptcoccus | $4 \times 10^6$ | Below detection limit |
|    | γ-streptcoccus | $2 \times 10^6$ | Below detection limit |

TABLE 2-continued

Result of culturing after spherical cleaning member was used to clean endoscope used to examine upper digestive tract (16 cases)

| Case No. | Kind of bacteria | Culturing immediately after examination | Culturing after endoscope was cleaned by sucking one spherical cleaning member with 20 cc of physiological saline solution |
|---|---|---|---|
| 13 | Neisserria sp | $1 \times 10^7$ | Below detection limit |
|  | Haemophilus sp | $2 \times 10^6$ | Below detection limit |
|  | Klebsiella pneumoniae | $1 \times 10^6$ | Below detection limit |
| 14 | α-streptcoccus | $6 \times 10^6$ | Below detection limit |
|  | Neisserria sp | $4 \times 10^6$ | Below detection limit |
| 15 | α-streptcoccus | $6 \times 10^7$ | Below detection limit |
|  | Neisserria sp | $2 \times 10^7$ | Below detection limit |
|  | Klebsiella pneumoniae | $1 \times 10^6$ | Below detection limit |
| 16 | α-streptcoccus | $2 \times 10^6$ | Below detection limit |
|  | Neisserria sp | $2 \times 10^6$ | Below detection limit |
|  | Haemophilus sp | $2 \times 10^5$ | Below detection limit |
|  | Klebsiella pneumoniae | $1 \times 10^4$ | Below detection limit |

As apparent from the above data, in all of the seven cases in which the endoscope was not cleaned with the cleaning member (porous member) of the present invention, some bacteria were cultured, whereas in all of the 16 cases in which the endoscope was cleaned with the cleaning member (porous member) of the present invention, the amount of bacteria was less than the detection limit.

Therefore the experimental results indicate that the cleaning method of sucking the cleaning member with the cleaning liquid is effective and reliable.

The cleaning member for a medical tube of the present invention is shaped like a spherical body having a porous fibrous structure formed of a large number of superfine fibers aggregated and intertwined three-dimensionally. The cleaning member moves along the lumen surface of the medical tube together with the cleaning liquid, while the cleaning member is wiping and cleaning the lumen surface of the medical tube.

Therefore according to the cleaning member, the superfine fibers are pressed against the surface of the duct of the endoscope. Consequently the cleaning member wipes and rubs off (chips off) secretions such as mucus, blood, tissue pieces, viruses, bacteria, and pollutants (including adsorbed oily content) such as various microbes from the surface of the duct of the endoscope and encloses them in porous portions between the superfine fibers.

The porous member for cleaning a treatment appliance insertion lumen of an endoscope is formed approximately spherically by molding a large number of superfine fibers; can be swelled with an aqueous cleaning liquid; an outer diameter thereof becomes larger than an inner diameter of the lumen to be cleaned, when the porous member swells; can be inserted into the lumen owing to a deformation thereof; and is movable in contact with an inner wall of the lumen by the aqueous cleaning liquid flowing into the lumen.

When the porous member is swelled with the cleaning liquid, the porous member deforms, and the outer diameter thereof becomes larger than the inner diameter of the lumen to be cleaned. Thus the porous member can be inserted into the lumen. The porous member moves inside the lumen, with the porous member in close contact with the inner wall of the lumen. Therefore the porous member is capable of securely removing pollutants (for example, secretion, bacteria, and the like) that have attached to the inner wall of the lumen. Since the porous member is deformable, it follows a change of the configuration of the lumen.

What is claimed is:

1. A cleaning instrument for a medical tube comprising:
   a cleaning member-holding plate having a plurality of holding-holes for holding a plurality of cleaning members fitted in said holes respectively, with said holding-holes disposed circumferentially at equal intervals; and
   a plurality of cleaning members shaped like a spherical body, having a porous fibrous structure formed of a large number of superfine fibers aggregated and intertwined three-dimensionally, which moves along a lumen surface of said medical tube together with a cleaning liquid, while said cleaning member is wiping and cleaning said lumen surface of said medical tube, and said cleaning members are accommodated in said through-holes respectively, and
   wherein an inner diameter of each of said holding holes at one end thereof is smaller than an outer diameter of said cleaning member, and an inner diameter of each of said holding-holes at the other end thereof is larger than said inner diameter thereof at said one end thereof.

2. A cleaning instrument for a medical tube according to claim 1, wherein said spherical body has a porous fibrous structure including flat superfine fibers, each having a sectional area of less than 10 $\mu m^2$.

3. A cleaning instrument for a medical tube according to claim 1, wherein said spherical body has a hard dense core part and a flexible rough part covering said hard dense core part.

4. A cleaning instrument for a medical tube according to claim 1, wherein said superfine fibers are of multi-layer division-type consisting of ethylene vinyl alcohol copolymer and polyethylene terephthalate.

5. A cleaning instrument for a medical tube according to claim 1, wherein said cleaning member has one or a plurality of linear portions having a predetermined thickness on an outer surface thereof.

6. A cleaning instrument for cleaning a treatment appliance insertion lumen of an endoscope comprising:
   a cartridge body having a plurality of through-holes disposed equiangularly or at equal intervals; and porous members, for cleaning a treatment appliance insertion lumen of an endoscope, which are formed approximately spherically by molding a large number of superfine fibers; can be swelled with an aqueous cleaning liquid; an outer diameter thereof becomes larger than an inner diameter of said lumen to be cleaned, when said porous member swells; can be inserted into said lumen owing to a deformation thereof; and are movable in contact with an inner wall of said lumen by said aqueous cleaning liquid flowing into said lumen, and said porous members are accommodated in a plurality of said through-holes respectively, and wherein an inner diameter of each of said through holes at one end thereof is smaller than an outer diameter of said porous member, and an inner diameter of each of said through holes at the other end thereof is larger than said inner diameter thereof at said one end thereof.

7. A cleaning instrument according to claim 6, wherein said porous member is approximately spherically formed by molding a large number of said superfine fibers intertwined three-dimensionally and removes pollutants that have attached to said inner wall of said lumen of said endoscope by capturing said pollutants onto a surface thereof and into an inside thereof.

8. A cleaning instrument according to claim 6, wherein said porous member has a core layer consisting of dense superfine fibers and an outer layer which covers said core layer and consists of superfine fibers not as dense as said superfine fibers of said core layer.

9. A cleaning instrument according to claim 6, wherein said superfine fibers include an ethylene vinyl alcohol copolymer, a composition of said ethylene vinyl alcohol copolymer and other thermoplastic polymers or substances formed by partly crosslinking said ethylene vinyl alcohol copolymer or said composition of said ethylene vinyl alcohol copolymer and said other thermoplastic polymers.

10. A cleaning instrument according to claim 6, wherein said superfine fibers are flat.

11. A cleaning instrument according to claim 6, wherein said porous member has one or a plurality of linear portions having a predetermined thickness on an outer surface thereof.

12. A cleaning instrument according to claim 6, wherein said cartridge body has not less than two through-holes; and said porous member is accommodated in each of not less than two through-holes.

13. A cleaning apparatus for cleaning a treatment appliance insertion lumen of an endoscope comprising:

a cleaning instrument, for cleaning said treatment appliance insertion lumen of said endoscope, having a cartridge body provided with a plurality of through-holes disposed equiangularly or at regular intervals; and lumen-cleaning porous members accommodated in said through-holes respectively; and a feeding instrument, for feeding said lumen-cleaning porous members, having a cleaning instrument accommodation portion removably accommodating said cleaning instrument, a cleaning liquid inflow side guide path communicating with one end of one through-hole of said cartridge body of said cleaning instrument accommodated in said cleaning instrument accommodation portion, a cleaning liquid outflow side guide path communicating with the other end of said through-hole, an endoscope-end mounting portion disposed at an end of said cleaning liquid outflow side guide path, and a cartridge-driving mechanism for operating said cartridge body in such a way that each through-hole of said cartridge body communicates with said cleaning liquid inflow side guide path and said cleaning liquid outflow side guide path, and wherein a diameter of said endoscope-end mounting portion increases toward an end thereof.

14. A cleaning apparatus according to claim 13, wherein said porous member is a cleaning member for a medical tube shaped like a spherical body, having a porous fibrous structure formed of a large number of superfine fibers aggregated and intertwined three-dimensionally, which moves along a lumen surface of said medical tube together with a cleaning liquid, while said cleaning member is wiping and cleaning said lumen surface of said medical tube.

15. A cleaning apparatus according to claim 13, wherein said lumen-cleaning porous members is formed approximately spherically by molding a large number of superfine fibers; can be swelled with an aqueous cleaning liquid; an outer diameter thereof becomes larger than an inner diameter of said lumen to be cleaned, when said porous member swells; can be inserted into said lumen owing to a deformation thereof; and is movable in contact with an inner wall of said lumen by said aqueous cleaning liquid flowing into said lumen.

16. A cleaning apparatus according to claim 13, wherein in a state where an end of said endoscope is mounted on said endoscope-end mounting portion, said endoscope-end mounting portion has a guide space, for guiding said lumen-cleaning porous member to said lumen, formed between an end of said endoscope and an inner surface of said endoscope-end mounting portion in such a way that an inner diameter of said guide space is larger than that of said cleaning liquid outflow side guide path and said lumen.

17. A cleaning apparatus according to claim 13, wherein said cartridge-driving mechanism drives said cartridge body stepwise at an angle between said adjacent through-holes or at an interval between said adjacent through-holes.

18. A cleaning apparatus according to claim 13, wherein an inner diameter of each of said through-holes at one end thereof is smaller than an outer diameter of said porous member, and an inner diameter of each of said through-holes at the other end thereof is larger than said inner diameter thereof at said one end thereof; and said cleaning instrument accommodation portion is capable of accommodating said cleaning instrument in such a way that the other side of said through-hole of said cleaning instrument is disposed at the side of said cleaning liquid outflow side guide path.

* * * * *